United States Patent [19]
Van Steenwyk et al.

[11] Patent Number: 4,605,560
[45] Date of Patent: Aug. 12, 1986

[54] OVIPOSITIONAL DISRUPTION OF THE NAVEL ORANGEWORM

[75] Inventors: Robert A. Van Steenwyk, Pleasanton; William W. Barnett, Clovis, both of Calif.

[73] Assignee: The Regents of The University of California, Berkeley, Calif.

[21] Appl. No.: 677,841

[22] Filed: Dec. 4, 1984

[51] Int. Cl.$^4$ ............................................. A01N 65/00
[52] U.S. Cl. ................................................... 424/195.1
[58] Field of Search ...................................... 424/195.1

[56] References Cited

U.S. PATENT DOCUMENTS

| | | | |
|---|---|---|---|
| 4,049,722 | 9/1977 | Jurd | 260/619 R |
| 4,198,533 | 4/1980 | Carney et al. | 568/840 |
| 4,228,093 | 10/1980 | Carney et al. | 556/482 |

OTHER PUBLICATIONS

Ortega, The Navel Orangeworm on Walnuts in Southern California, 1950, Diamond Walnut New, 32(5):6–7.
Post et al., Tendencies of Navel Orangeworm Infestations in Almonds, 1959, Almond Facts, 24(1):4, 12.
Wade, Biology of the Navel Orangeworm . . . on Almonds and Walnuts in Northern California, 1961, Hilgardia, 31(6):129–171.
Price et al., Chemical Attractants for Navel Orangeworm Moths, 1967, California Agriculture 21(11):10–11.
Caltagirone et al., Almond Sticktights Contribute to Navel Orangeworm Infestations, 1968, California Agriculture 22(3):2–3.
Rice et al., Egg Traps for the Navel Orangeworm . . . , 1976, Environmental Entomology 5:697–700.
Vité, Southern Pine Beetle, Effect of Aerial Pheromone Saturation on Orientation, 1976, Naturwissenschaften 63:44.
Curtis et al., Oviposition and Development of the Navel Orangeworm in Relation to Almond Maturation, 1977, J. Econ. Entomol. 70:395–398.
Curtis et al., Response of Navel Orangeworm Moths to Attractants Evaluated as Ovipositional Stimulants in an Almond Orchard, 1979, Environmental Entomology, 8:330–333.
Buttery et al., Components of Almond Hulls: Possible Navel Orangeworm Attractants and Growth Inhibitors, 1980, Agricultural & Food Chemistry, 353–356.
Buttery et al., 2-Hexyl-3-methylmaleic Anhydrides . . . , 1980, Agricultural & Food Chemistry, 28:1336.
Andrews et al., Differential Attractiveness of Infested and Uninfested Mummy Almonds to Navel Orangeworm Moths, 1982, Environmental Entomology 11:280–282.
Rice, R. E., A Comparison of Monitoring Techniques for Navel Orangeworm, 1976, J. Econ. Entomol., 69(1):25–28.
Goodwin, James A., et al., The Mating and Oviposition Behavior of the Navel Orangeworm, *Paramyelois transitella* (Walker), 1964, Hilgardia, 35(18):507–523.

*Primary Examiner*—Albert T. Meyers
*Assistant Examiner*—John W. Rollins, Jr.
*Attorney, Agent, or Firm*—Owen, Wickersham & Erickson

[57] ABSTRACT

A method for obtaining ovipositional disruption of navel orangeworm. The air of nut orchard area, e.g., almonds, where egg-laying by the moth of the navel orangeworm is expected is permeated, as by spraying, by a composition of matter incorporating as an active ingredient as effective amount of crude almond oil. The composition may be a water emulsion of crude almond oil or may be a water emulsion of a wettable powder formulation containing appreciably equal amounts of crude almond oil and ground almond press cake.

7 Claims, No Drawings

OVIPOSITIONAL DISRUPTION OF THE NAVEL ORANGEWORM

This invention relates to ovipositional disruption of the navel orangeworm.

BACKGROUND OF THE INVENTION

The navel orangeworm, *Amyelois transitella* (Walker), is the most serious field insect pest of almonds in California. Growers lost about $24 million to this insect in 1977, an average of $87 per bearing acre.

Several researchers have tested a variety of substances for attracting female moths to a trap. Rice et al. (1976) reported on egg traps baited with a mixture of wheat bran, glycerine, honey, and water that both attracted female moths and stimulated oviposition. (Rice, R. E., L. L. Sadler, M. L. Hoffman, and R. A. Jones, 1976. Egg traps for the navel orangeworm, *Paramyelois transitella* (Walker). Environmental Entomology 5: 697-700.) In an effort to find a substance that could be used to attract navel orangeworm moths to traps, Price et al. (1967) screened about 225 organic compounds and found phenyl propionate the most efficacious. (Price, D. W., J. A. Mazrimas, and F. M. Summers, 1967. Chemical attractants for navel orangeworm moths. Calif. Agric. 21(11): 10-11.) Five other compounds that consistently showed a relatively high degree of attractiveness were phenyl isobutyrate, phenyl-2-propanone, phenyl ether, α-methylbenzyl alcohol, and ethyl phenylacetate. About 90-95% of the moths attracted to these chemicals were female.

The attraction of female *A. transitella* to previously damaged host material (walnuts) was noticed by Ortega (1950). (Ortega. J. C. 1950. The navel orangeworm on walnuts in southern California. Diamond Walnut News 32(5):6-7.) Later Caltagirone et al. (1968) and Curtis and Barnes (1977) reported that female moths deposited 2.4 and 2.0-fold, respectively, more eggs on previously infested than on uninfested old nuts. (Caltagirone, L. E., D. W. Meals, and K. P. Shea. 1968. Almond sticktights contribute to navel orangeworm infestations. Calif. Agric. 22(3):2-3.) (Curtis, R. K., and M. M. Barnes. 1977. Oviposition and development of the navel orangeworm in relation to almond maturation. J. Econ. Entomol. 70. 395-8.) These data apparently indicate that host odors may be more important than are tactile stimuli in the oviposition behavior of *A. transitella*. However, when Post et al. (1959) investigated whether the navel orangeworm was a pest of stored almonds, they concluded that almonds were not much more attractive to the female moths than were the building materials of the cage used in the test. (Post, G. R., D. J. Hurlebaus; and F. M. Summers. 1959. Tendencies of navel orangeworm infestations in almonds. Almond Facts 24(1): 4, 12.) Also, Wade (1961) reported that large numbers of navel orangeworm eggs were occasionally laid on twigs several inches from the nearest nut but never on branches or leaves. (Wade, W. H. 1961. Biology of the navel orangeworm, *Paramyelois transitella* (Walker), on almonds and walnuts in northern California. Hilgardia 31(6): 129-71.)

A great deal of published information concerns the use of insect sex pheromones to disrupt communication between male and female insects of the same species so that they cannot find one another for the purpose of mating. For example, see Andrews, Keith L. and Martin M. Barnes, 1982, Differential Attractiveness of Infested and Uninfested Mummy Almonds to Navel Orangeworm Moths, Environmental Entomology 11:280-282, and Buttery, Ron G., E. L. Soderstrom et al., Components of Almond Hulls: Possible Navel Orangeworm Attractants and Growth Inhibitors, 1980 Agricultural & Food Chemistry 353-356, and Buttery, Ron G., R. M. Seifert et al., 2-Hexyl-3-methylmaleic Anhydride: An Unusual Volatile Component of Raisins and Almond Hulls, 1980, Agricultural & Food Chemistry 28:1336. Further, see Carney et al. U.S. Pat. Nos. 4,198,533, Apr. 15, 1980 and 4,228,093, Oct. 14, 1980. There are a number of commercially available such products.

Other research (Curtis, C. E., and Clark, J. D., 1979, Response of Navel Orangeworm Moths to Attractants Evaluated as Oviposition Stimulants in an Almond Orchard, Environmental Entomology 8:330-333.) was designed to determine whether extracts of frass, larvae, and almond-fruit-parts contained attractive substances that could be extracted by using several different solvents.

SUMMARY OF THE INVENTION

Navel orangeworm populations in almonds have been controlled according to the present invention by the application to an almond orchard of almond by-products, such as by spraying a water emulsion of crude almond oil or an emulsion of a wettable powder formulation of almond press cake and crude almond oil.

Crude almond oil is expressed from rejected almonds. This oil is then refined and sold as a premium cooking oil. The press cake is the remains of the rejected almonds after the oil has been expressed. It is sold as cattle feed. Early tests indicated that refined almond oil is much less effective than the crude almond oil.

Initial studies employed (1) 5 gallons per acre of crude almond oil emulsified with 2% Triton X-363M applied as a spray with 100 gallons of water per acre or else (2) 2 pounds per acre of a wettable powder formulation of crude almond oil plus almond press cake (30% crude almond oil, 30% almond press cake, 20% Microcel E, 10% Attaclay, 4% Lignosite, 4% I Gypson TN-74, 2% Dispersant NI-O) applied as a spray with 100 gallons of water per acre. These gave nearly complete suppression of egg-laying for three weeks on a small test area. The mixture of crude almond oil and almond press cake may actually be ground rejected almonds or (and usually preferably) a reconstitution thereof made by expressing the oil from the rejected almonds, then grinding what remains to obtain the powdered press cake, and then mixing the oil and the press cake together.

In later tests using large plots (5 to 20 acres each), 5 gallons of emulsified almond oil in 100 gallons of water were applied by commercial spray equipment. This application demonstrated a nearly complete suppression of egg-laying and 60-90% control of larval infestations.

This control compares quite favorably to that achieved with conventional insecticides, such as Sevin or Guthion, which typically give 40-60% control. The estimated cost of the final product on a per acre basis is substantially lower than that of conventional insecticides. Preferably, two, three, or four applications of the almond by-product are used to achieve control.

To our knowledge there are no published accounts of a by-product of a plant species being used to disrupt oviposition of an insect pest of that plant species. The only article remotely similar to our studies was that of Vité (1976) in which both sex pheromone and host terpene (α-pinene) were combined and *unsuccessfully* tested in the disorientation of the southern pine beetle. (Vité, J. P. Southern Pine Beetle: Effect of Aerial Pheromone Saturation on Orientation. Naturwissenschaft 63 (1976) page 44.)

Ovipositional disruption is similar in concept to mating disruption in that the purpose of both is to permeate the air with an odor of a certain object in order to make it impossible for the insect to locate that object by flying toward its odor. To disrupt navel orangeworm oviposition according to the present invention, the air surrounding the almond tree is permeated with the odor of almond nut, which is the ovipositional stimulant, by spraying the tree or orchard with materials including as the active ingredient crude almond oil or powdered almond press cake plus crude almond oil. The female then is apparently unable to "smell" the nut (mummy or sound-split) on which to oviposit.

Preferably, the material is applied early in the spring during the first ovipositional period when the available ovipositional sites and populations are low to make it difficult for the navel orangeworm to reproduce. They may also be applied at hull-split time to protect the sound nuts and lessen the severity of infestation.

We have investigated phytotoxicity of almond oil to almond foliage and ovipositional disruption using in some tests an emulsified crude almond oil and in others a wettable powder formulation of powdered almond press cake and crude almond oil (reconstituted ground rejected almonds).

PHYTOTOXICITY TRIALS

Example 1

The phytotoxic reaction of crude almond oil to almond foliage was evaluated by spraying, to run-off, individual branches of 3-year-old Nonpareil almond trees with crude almond oil at a rate of 20, 10, 5, 2½, or 1¼ gallons of crude almond oil per 100 gallons of water with no emulsifier added. The treatments were applied in August. The trees were visually observed for phytotoxic reaction to the oil for the remainder of the season.

There were visible oil droplets on the leaves at any of the stated rates of oil. At the 20 and 10 gallon rates, the leaves seemed to come off the trees more easily, but there were no typical phytotoxic reactions. There was intermediate effect at the 5 gallon rate and no effect at the 2½ and 1¼ gallon rates. From this preliminary study, it appeared that oil did not cause an acute phytotoxic reaction.

Example 2

A more thorough study on the phytotoxic reaction of almond oil was then conducted. Individual Nonpareil and Carmel almond trees were sprayed to run-off with 5, 2, or 1¼ gallons crude almond oil per 100 gallon water, per acre. The oil contained 2% emulsifier Triton X-363M and was applied in late April with a hand-held orchard sprayer operating at 300 psi. The amount of oil/water mixture sprayed per individual tree was 2-3/16 gallons, or about 250 gal/acre. The trees were visually observed for phytotoxic reaction to the oil until June 1. There were visible oil droplets on the leaves at all rates of oil; however, no phytotoxic reaction was observed.

Example 3

The following year, when a spray with rate of 5 gallons oil per 100 gallons of water with 2% emulsifier, per acre, a phytotoxic burn of the foliage and some leaf drop was observed. It is not clear whether it was the result of different oils in the two years of study or the condition of the leaves. The oil was applied to young foliage in April and May.

OVIPOSITIONAL DISRUPTION TRIALS

Example 4

An ovipositional disruption study was conducted in a Nonpareil, Merced, and Thompson almond orchard in Chowchilla, CA. Three treatments were replicated 4 times in a randomized complete block design. The treatments here were (1) 4 gallons per acre of crude almond oil plus 1% emulsifier Triton X-363M, and (2) 2 pounds per acre of a wettable powder formulation of 30% crude almond oil, 30% ground press cake, and 40% inert ingredients, and (3) an untreated control. Each replicate was 12 rows wide by 9 trees along, about 1.4 acres. The materials were applied on July 29 as the Nonpareils began to split and again on Aug. 30 as the Merceds and Thompsons began to split. They were applied with Best Air blast orchard sprayer operating at 100 psi with a delivery rate of 100 gallons of water per acre. Except for a dormant spray, no insecticides had been applied to the orchard.

The plots were monitored for navel orangeworm activity by inspecting 100 nuts per plot weekly after 100% hull-split (8/15 through 9/26). The nuts were collected from the center of each plot. The first two collections were from the Nonpareil variety and the last four from the Merced variety. The final harvest was 250 nuts per plot. There was no final harvest of the Nonpareil variety because the grower harvested and picked up the nuts without informing the investigators.

Ovipositional activity of the navel orangeworm was monitored by placing 3 standard egg traps in each plot and inspecting the traps twice a week. The exact date the egg traps were inspected varied somewhat because of irrigation in the orchard. The grower did not want anyone to enter the orchard when it was wet.

Ovipositional activity, as measured by the egg traps, was quite low in all plots after the initial application on July 29 (Table 1). The activity increased during August, reaching a peak of 14.6 eggs per trap per day on Aug. 30, the trap counts decreased to a very low level, even in the untreated plots, and remained low for the rest of the season. This rapid drop in egg deposition in the untreated check is difficult to explain and was not expected since ovipositional activity should have continued to increase. One possible explanation is that the oil or oil plus press cake treatment disrupted ovipositional activity of the moths over the entire plot. If so, the plot size was too small, a phenomenon well known in pheromone disruption studies where large plots are needed to assess the effectiveness of the pheromone. However, it was not expected that this would be the case with almond oil, since it should be less volatile than most pheromones.

TABLE 1

Ovipositional disruption of navel orangeworm by almond oil or almond oil plus press cake, as measured by egg traps

| Treatment | Mean* number of NOW eggs per trap per day on: | | | | | | | | | |
|---|---|---|---|---|---|---|---|---|---|---|
| | 8/8 | 8/17 | 8/22 | 8/25 | 8/29 | 9/7 | 9/12 | 9/16 | 9/19 | 9/23 |
| Untreated | 0 a | 0.09 a | 0.67 a | 2.03 b | 8.12 b | 1.04 a | 0.70 a | 0.46 a | 1.03 a | 0.44 a |
| Oil | 0 a | 0.02 a | 0.58 a | 3.92 a | 9.70 ab | 0.63 a | 0.62 a | 0.27 a | 0.50 a | 0.52 a |
| Oil + press cake | 0.01 a | 0.08 a | 1.18 a | 2.97 ab | 14.62 a | 0.21 a | 0.13 a | 0.40 a | 1.55 a | 1.29 a |

*Means followed by the same letter in a vertical column are not significantly different at the 5% level (DMRT).

Nut infestation (Table 2) showed a pattern similar to egg deposition on traps. Infestation in the first sample from Nonpareil trees was low and by the second sample, one month after application, the amount of infestation began to increase. The Nonpareil nuts were then commercially harvested and nut samples were taken from Merced trees. The first two samples from the Merced trees again had low infestation; however by the third sample, the infestation had begun to increase and by the fourth, or final harvest sample, the infestation exploded, reaching a peak of 42% in the oil plus press cake plots. Perhaps the oil or oil plus press cake suppressed oviposition over the entire experiment, but the plot size was too small for one to know. It appears that the oil or oil plus press cake suppressed oviposition or nut infestation for 3 weeks and the large increase in nut infestation 4 weeks after application resulted from a large population of navel orangeworm in the orchard and the dissipation of the the odor from the oil or oil plus press cake treatment.

TABLE 2

Ovipositional disruption of navel orangeworm by almond oil or almond oil plus press cake, as measured by nut infestation

| Treatment | Mean* percent NOW-infested nuts on: | | | | | |
|---|---|---|---|---|---|---|
| | Nonpareil 8/15 | Nonpareil 8/22 | Merced 9/7 | Merced 9/12 | Merced 9/19 | Merced 9/26 |
| Untreated | 0 a | 2.0 a | 0.5 a | 0.3 a | 5.0 a | 39.0 ab |
| Oil | 0 a | 0.5 a | 1.8 a | 0.8 a | 2.5 a | 32.3 b |
| Oil + press cake | 1.0 a | 2.5 a | 0.8 a | 1.0 a | 4.3 a | 42.0 a |

*Means followed by the same letter in a vertical column are not significantly different at the 5% level (DMRT).

Example 5

In another test, four orchards, 10 to 40 acres in size, were split into two equal parts. On one part 5 gallons of crude almond oil with 2% emulsifier (Triton X-363M) per acre were applied. The other part was left untreated. No insecticides were applied to any of the orchards during the entire season.

The five gallons of crude almond oil emulsified with 2% Triton X-363M were applied with 100 gallons of water per acre with a commercial air blast sprayer.

Standard Zoecon navel orangeworm egg traps were painted black and baited with 15 grams of ground almond press cake+10% crude almond oil by weight. Eight egg traps were placed in a uniform manner through each side of each orchard. Traps were placed in the orchards on March 29 and monitored twice a week until June 4–7. Mummy nuts were sampled on May 30–June 1 by searching each side of each orchard for a maximum of 8 man-hours. At commercial harvest, 1000 nuts from each side of each orchard were inspected for damage.

Orchard No. 1 was a 40-acre block of 10-year-old Thompson and Merced, one to one, with tree spacing of 20 feet and row spacing of 22 feet. The southern portion (about 20 acres) was treated on April 23. for the first two tanks, about 2 gallons oil per acre rather than 5 gallons per acre was applied, because of improper calibration of equipment. In the last two tanks, the oil formed an inverse emulsion; thus very little oil was applied with these tanks. This orchard was *not* used in the analysis because of the application problem.

Navel orangeworm, egg traps were placed in the orchard on March 29 and monitored until June 4. Mummy nut samples were collected on May 30, and final harvest samples were collected on Sept. 11.

Orchard No. 2 was a 40-acre block of 10-year-old Nonpareil and Carmel, one to one, with tree spacing of 22 feet and row spacing of 24 feet. The northern portion (20 acres) was treated on April 30.

The egg traps were placed in the orchard on March 29 and monitored until June 7. Mummy nut samples were collected on May 29, and final harvest samples were collected on Aug. 17.

Orchard No. 3 was a 30-acre block of 10-year-old Nonpareil and Carmel, one to one, with tree spacing of 22 feet and row spacing of 24 feet. The southern portion (about 15 acres) was treated on April 30.

The egg traps were placed in the orchard on March 29 and monitored until June 7. Mummy nut samples were collected on May 29, and final harvest samples were collected on Aug. 2.

Orchard No. 4 was a 10-acre block of 15-year-old Thompson and Mission, one to one, with tree spacing of 22 feet and row spacing of 22 feet. The eastern portion (about 5 acres) was treated on May 1. Because of the inverse emulsion problem, additional emulsifier, about 1 pint (Joy soap), was added to each 250 gallon tank.

The egg traps were placed in the orchard on March 29 and monitored until June 7. Mummy nut samples were collected on May 30, and final harvest samples were collected on Aug. 29.

In all orchards except No. 1, there was a nearly complete suppression of oviposition of the navel orangeworm for the entire spring after the oil application (Table 3). When the percent of eggs per trap per day was analyzed, there was no significant difference in the percentages before treatment, while there was a significant decrease of 82% after treatment (Table 4).

TABLE 3

NOW oviposition on traps in almond orchards
treated with crude almond oil

| | Mean number of eggs/trap/day | | | |
|---|---|---|---|---|
| | Before Treatment | | After treatment | |
| Orchard | Treated | Untreated | Treated | Untreated |
| No. 1 | 1.9 | 4.1 | 1.9 | 4.9 |
| No. 2 | 0.9 | 1.7 | 0.4 | 1.9 |
| No. 3 | 3.2 | 4.3 | 0.2 | 2.3 |
| No. 4 | 8.4 | 10.1 | 0.4 | 14.3 |

TABLE 4

NOW oviposition on traps in almond orchard
treated with crude almond oil
(without No. 1)

| | Mean number of eggs/trap/day | |
|---|---|---|
| | Before Treatment | After treatment |
| Treated | 41 a | 9 a |
| Untreated | 59 a | 91 b |

Data analyzed with the arcsin transformation. Means followed by the same letter are not significantly different at the 5% level (Student's Paired T-test).

There was a corresponding decrease of about 83% in the number of infested mummy nuts (Tables 5 and 6). This decrease probably would have been more dramatic had the oil been applied earlier in the spring or had two applications been made.

TABLE 5

Infested mummy nuts in almond orchards
treated with crude almond oil

| | Treated | | Untreated | |
|---|---|---|---|---|
| Orchard | No. nuts inspected | % nuts infested | No. nuts inspected | % nuts infested |
| No. 1 | 67 | 31.4 | 34 | 47.1 |
| No. 2 | 10 | 0 | 16 | 6.3 |
| No. 3 | 14 | 0 | 19 | 10.5 |
| No. 4 | 88 | 5.7 | 130 | 17.7 |

TABLE 6

Infested mummy nuts in almond orchards
treated with crude almond oil
(without No. 1)

| | Mean No. nuts inspected | Mean* % nuts infested |
|---|---|---|
| Treated | 37.3 | 1.9 a |
| Untreated | 55.0 | 11.5 b |

*Data analyzed with the arcsin transformation. Means followed by the same letter are not significantly different at the 5% level (Student's Paired T-test).

In the final nut harvest, there was no difference in percent infestation between the treated and untreated portions of the orchards (Table 7). However, very few navel orangeworm were found at harvest in either the treated or untreated portions of the orchards.

TABLE 7

Infested sound nuts in almond orchards
treated with crude almond oil

| | % infested nuts* | |
|---|---|---|
| Orchard | Treated | Untreated |
| No. 1 | 0.7 | 0.5 |
| No. 2 | 2.0 | 1.8 |
| No. 3 | 0.5 | 0.4 |
| No. 4 | 0.5 | 0.1 |

*Based on a 1000-nut sample.

DISCUSSION

The four orchards were selected because all had high mummy nut infestations and the growers would not treat during the spring. However, a high wind storm on about April 26 caused a large drop in the number of mummy nuts. Thus, mummy nuts in all orchards except No. 4 were quite low and one had to search for a considerable period of time to collect even a low number.

CONCLUSIONS

Crude almond oil does not appear to be phytotoxic to the almond tree at commercially acceptable rates of application. It does show some effect at higher rates (10-20 gallons per 100 gallons of water).

The crude almond oil appears to suppress oviposition for 3 to 4 weeks after application.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A method for obtaining ovipositional disruption of navel or orangeworm, comprising
   permeating the air of an almond orchard area where egg-laying by the moth of the navel orangeworm is expected, by a composition of matter incorporating as an active ingredient an effective amount of a water emulsion of crude almond oil.

2. The method of claim 1 also incorporating an effective amount of almond press cake.

3. A method of obtaining ovipositional disruption of navel orangeworm, comprising
   spraying an almond orchard area infested by navel orangeworm with a water emulsion of crude almond oil.

4. The method of claim 3 wherein the emulsion is at the rate of about 5 gallons of crude almond oil per 100 gallons of water, per acre.

5. A method of ovipositional disruption of navel orangeworm, comprising spraying an almond orchard area with a water emulsion of a wettable powder formulation containing approximately equal amounts of crude almond oil and ground almond press cake.

6. The method of claim 5 having about two pounds of said wettable powder, with 30% of said powder being crude almond oil and 30% being ground almond press cake, per 100 gallons of water.

7. The method of claim 5 wherein said crude almond oil and ground almond press cake are reconstituted almond rejects.

* * * * *